United States Patent [19]

Patel

[11] 4,007,005
[45] Feb. 8, 1977

[54] HAIR SETTING COMPOSITIONS WHICH DISPLAY HIGH RESISTANCE TO HIGH HUMIDITY

[75] Inventor: Kanu I. Patel, Chatsworth, Calif.

[73] Assignee: Redken Laboratories, Inc., Van Nuys, Calif.

[22] Filed: June 19, 1975

[21] Appl. No.: 588,383

[52] U.S. Cl. .......................... 8/127.51; 424/DIG. 1; 424/DIG. 2; 424/47; 424/71; 424/78; 424/80
[51] Int. Cl.² .......................................... A61K 7/11
[58] Field of Search ................. 424/DIG. 1, DIG. 2, 424/47, 80, 71, 78; 8/127.51

[56] References Cited

UNITED STATES PATENTS

| | | | |
|---|---|---|---|
| 2,723,248 | 11/1955 | Wright | 424/47 X |
| 3,849,548 | 11/1974 | Grand | 424/70 |

*Primary Examiner*—Albert T. Meyers
*Assistant Examiner*—Vera C. Clarke
*Attorney, Agent, or Firm*—Christie, Parker & Hale

[57] ABSTRACT

Aqueous solutions of water soluble, reactive polyamide-epichlorohydrin resins and vinylpyrrolidone polymers serve upon application to hair as a spray or lotion to markedly improve the resistance of set curls to relaxation under conditions of high humidity.

14 Claims, No Drawings

HAIR SETTING COMPOSITIONS WHICH DISPLAY HIGH RESISTANCE TO HIGH HUMIDITY

BACKGROUND OF THE INVENTION

It is well known to set curls in the home or salon by sprays or lotions. As opposed to sets induced by a permanent wave, they are temporary in nature, intended to last only until the next shampoo. Because the ingredients applied are, by necessity, water sensitive to some degree, under conditions of high humidity, particularly at higher ambient temperatures, the curls will relax due to the attack of atmospheric moisture on the film coating on the hair strands added by the spray or lotion. In many instances, once the protective set becomes undermined, the hair will continue to absorb moisture, relax and become limp.

SUMMARY OF THE INVENTION

According to the present invention, there is provided an unusually effective composition for use in aerosol and non-aerosol hairsprays and hair setting lotions which exhibit an unusual resistance to moisture attack under conditions of high humidity as aggravated by elevated ambient temperature.

The compositions comprise a mixture of at least one water soluble, reactive polyamide-epichlorohydrin resin in combination with at least one water soluble, vinylpyrrolidone polymer in solution with a solvent carrier therefore. The resin and polymer are present in an amount sufficient to induce upon evaporation of the solvent resistance to curl relaxation, but insufficient to form a tacky film or one which will flake from the hair strands. The particularly preferred water soluble, reactive polyamide-epichlorohydrin resins are those formed by the reaction of epichlorohydrin with the polymer formed by the reaction of adipic acid and diethylene triamine.

Depending on end use application and the degree set desired, the composition may contain from about 0.5 to about 8%, preferably about 1 to about 4% each of the water soluble, reactive polyamide-epichlorohydrin resin, and vinylpyrrolidone polymer. It is preferred that the weight ratio of the water soluble, reactive polyamide-epichlorohydrin resin to vinylpyrrolidone polymer be from about 1:2 to 2:1, with a total solids content of resin and polymer from about 1 to about 5% by weight based on the total weight of the resin, polymer and solvent carrier.

A suitable solvent carrier is typically a water-ethanol blend containing about 85% ethanol and about 15% water. Other ratios and solvent carrier compositions may be readily employed.

The compositions of this invention can be applied to the hair as an aerosol spray using conventional propellants, as a non-aerosol spray from a container using a plunger type pump, or as a liquid setting solution.

Upon evaporation of the solvent-carrier, the resin and polymer interact synergistically to impart unusually effective resistance to humidity as compared to the resin and polymer constituents of the composition alone.

Other ingredients used in the styling and setting of hair may be included, such as perfumes, proteins, modified alcohol soluble hair conditioners, plasticizers and the like.

DETAILED DESCRIPTION

The present invention pertains to compositions comprising a mixture of a reactive polyamide-epichlorohydrin resin, and a water soluble vinylpyrrolidone polymer in a suitable solvent carrier for application to the hair as an aerosol or non-aerosol spray and setting solution, which upon evaporation of the solvent carrier imparts unusual resistance to relaxation of hair curls under conditions of high temperature and humidity.

As used herein the term "water soluble, reactive polyamide-epichlorohydrin resins," there is meant resins derived from the reaction of epichlorohydrin with a polyamide polymer obtained by reaction of a polyalkylene polyamide with a saturated dicarboxylic acid. The resins have the general formula:

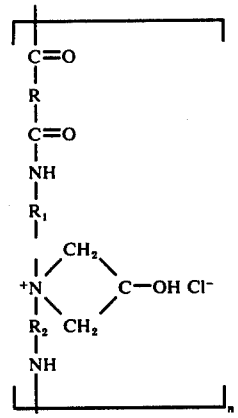

wherein R is an alkyl group containing from 1 to about 6 carbon atoms, $R_1$ and $R_2$ are independently alkyl groups containing at least 2 and preferably from about 2 to about 4 carbon atoms, and n is the number of repeating units in the molecule. Each alkyl group may be straight or a branched chain.

The presently preferred water soluble reactive polyamide-epichlorohydrin resins are formed by the reaction of epichlorohydrin with the reaction product of diethylene triamine and adipic acid. Mixtures of resins may be used.

In the resin, the chlorine may be replaced by other anions, such as phosphate which do not alter the reactive nature of the cationic thermosetting resins.

The preparation of the water soluble, reactive polyamide-epichlorohydrin resins are described in detail in U.S. Pat. No. 3,227,615 issued Jan. 4, 1966 incorporated herein by reference.

By the term "water soluble vinylpyrrolidone polymer," as used herein is meant homopolymers and copolymers of vinylpyrrolidone as well as mixtures thereof. While the comonomers can vary widely so long as solubility is not adversely effected, the presently preferred comonomer is vinyl alcohol.

As evidenced from the above referenced U.S. Pat. No. 3,227,615, water soluble polyamide-epichlorohydrin resins have been used in combination with bisulfites in permanent hair waving compositions. The resin in the reactive state, however, is too highly reactive towards the hair for direct application to the hair in appreciable amounts, as active sites on the hair will tend to open the functional ring and induce a permanent bond which resists removal by shampooing. In smaller amounts, the set begins to relax under humid conditions after a fairly short exposure time.

Polyvinylpyrrolidone polymers, because they are hygroscopic are readily affected by ambient moisture and become tacky. Vinylpyrrolidone polymers while effective to cause a set will, under humid conditions, yield to moisture action and the curl will totally relax.

Quite surprisingly, the two combine synergistically to provide unusual resistance to the effects of elevated ambient temperature and humidity, and remain unaffected by exposure to a relative humidity of 80 to 85% at temperatures of 80° to 90° F, for at least a day and substantially unaffected for several days.

Despite the unusual resistance to high humidity even under conditions of elevated temperatures, the compositions are nevertheless readily removed from the hair by conventional shampooing to restore the hair once more to the condition it was in prior to the application of the temporary set.

The compositions of this invention are provided as a mixture of the water soluble reactive, polyamide-epichlorohydrin resin and the water soluble vinylpyrrolidone polymer, and a suitable solvent carrier therefore. The solids content, i.e. resin plus polymer are sufficient under normal application to induce resistance to humidity without becoming tacky or brittle (flaky).

Generally, the reactive, water soluble polyamide-epichlorohydrin resin and vinylpyrrolidone polymers may each be employed in the composition in an amount from about 0.5 to about 8% or more by weight based on the total weight of the composition. The preferred range for most applications is from about 1 to about 4% by weight. Actual amounts will depend on the set desired as hereinafter explained.

While not narrowly critical, it is preferred that the weight ratio of the water soluble, reactive polyamide epichlorohydrin resin to vinylpyrrolidone polymer be in the range of about 1:2 to about 2:1. In this range, the net combination of resins provides the most desired properties of resistance to an attack of moisture under conditions of high temperature and humidity, while permitting the hair to retain its desired feel.

While any suitable solvent carrier for the resin and polymer blend may be used for application to the hair, the conventional solvent carriers are water based and typically a mixture of an alcohol and water. Although any water soluble alcohol of low vapor pressure may be used, ethanol because of availability in an odor free state is preferred. Other alcohols, such as isopropanol may be used if a masking agent is employed as part of the composition. The preferred solvent carrier is a blend of about 15% by weight water and about 85% by weight ethanol.

Besides the basic ingredients of the composition, namely the water soluble, reactive polyamide-epichlorohydrin resin, vinylpyrrolidone polymer and the solvent-carrier, there may be included other ingredients well known to be contained in hair setting sprays and lotions. These include perfumes, proteins, hair conditioners such as Penthenol $^{TM}$, a modified alcohol, as well as plasticizers, such as propylene glycol, dibutylphthalate, glycerin and the like. When used, plasticizers are generally present in a weight ratio of about 10:1 parts by weight the total resin per part by weight plasticizer. If the composition is used as a setting rinse, there may be added soluble dyes or brighteners to enhance the quality of the hair during the lifetime of the temporary set.

A most expeditious way to apply the compositions of the invention is by way of a non-aerosol spray in which the compositions are dispensed from a container by action of a finger actuated spray pump. It may also be employed in an aerosol spray using fluorocarbons; hydrocarbon, such as isobutane, and propane-isobutane blends; carbon dioxide and like propellants.

Depending upon a degree of hold desired, the total solids content (resin plus polymer) of the applied composition will vary. In spray application and for a soft hold, the typical total resin concentration will normally be about 1 to 2% by weight solids. For normal hold, solids content will be about 3 to 4%, and for a firm hold will be about 5% or more. When used as a solution because of a higher level of application of solids to the hair, the compositions are diluted below above those levels, generally to about 50% of the above levels.

While no wise limiting, the following example is illustrative of the unique holding properties of the composition of this invention.

EXAMPLE 1 AND CONTROLS

Five swatches of brown tinted human hair of common origin, each seven inches long and weighing one gram were used. Each was immersed in 10 cc of a test setting solution as described below for three minutes, then rolled over a ½ inch roller and dried under a salon dryer maintained at 130° F (air temperature) for 0.5 hour. The rollers were removed and the rolled set swatches of hair placed in a controlled humidity chamber. Chamber temperature was maintained at 80° to 90° F and at a relative humidity of 80 to 85%. Percent of curl relaxation was measured at various time intervals.

To illustrate the utility of the compositions of this invention (Example 1), the setting solution contained 2.16% by weight DELSETTE 101, a water soluble, reactive polyamide-epichlorohydrin resin manufactured and sold by Hercules Powder Company, 1.90% by weight of a polyvinylpyrrolidone polymer known as PVP K-30, manufactured by General Analine and Film Corporation, 81.5% by weight ethanol and 14.4% by weight water. A mixture of 85% by weight ethanol and 15% by weight water (ethanol-water mixture) served as the diluent carrier.

For Control A, there was used a 2.16% by weight solution of DELSETTE 101 in the ethanol-water mixture. This corresponded to the concentration of the water soluble, reactive polyamide-epichlorohydrin resin in the total composition of Example 1.

For Control B, there was used a 1.9% by weight solution of PVP K-30 in the ethanol-water mixture. This corresponded to the concentration of the polyvinylpyrrolidone in the total composition of Example 1.

For Control C, there was used a 4.06% by weight solution of DELSETTE 101 in the ethanol-water mixture. This corresponded to total resin content in the composition of Example 1.

For Control D, there was used a 4.06% by weight solution of PVP K-30 in the ethanol-water mixture, again corresponding to the total resin content in the composition of Example 1.

The results of the Humidity Test are shown in Table I.

TABLE I

| Example or Control | % CURL RELAXATION — Time in Hours | | | | | | |
|---|---|---|---|---|---|---|---|
| | 1 | 2 | 4 | 22 | 29 | 262 | 265 |
| Example 1 | 0 | 0 | 0 | 1.0 | 1.0 | 5.0 | 5.0 |
| Control A | 5.0 | 5.0 | 10.0 | 15.0 | 15.0 | 15.0 | 15.0 |
| Control B | 40.5 | 95.0 | 100.0 | 100.0 | 100.0 | 100.0 | 100.0 |
| Control C | 7.5 | 10.5 | 10.5 | 20.0 | 25.0 | 25.0 | 25.0 |
| Control D | 1.0 | 85.0 | 100.0 | 100.0 | 100.0 | 100.0 | 100.0 |

What is claimed is:

1. A sprayable temporary curl setting composition comprising at least one water soluble, reactive polyamide-epichlorohydrin resin having the formula:

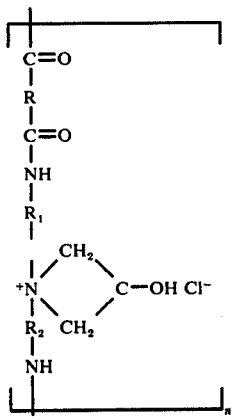

wherein R is an alkyl group containing from 1 to about 6 carbon atoms, $R_1$ and $R_2$ are independently alkyl groups containing at least 2 carbon atoms, and n is the number of repeating units in the water soluble molecule and at least one water soluble vinylpyrrolidone polymer dissolved in a solvent-carrier for said resin and polymer, wherein the resin and polymer concentration of said composition are independently from about 0.5 to about 8 percent by weight based on the weight of resin, polymer and solvent-carrier and wherein the weight ratio of resin to polymer is from about 1:2 to about 2:1.

2. The composition of claim 1 in which the resin is present in an amount of from about 1 to about 4 percent by weight based on the weight of resin, polymer and solvent-carrier.

3. The composition of claim 1 in which the vinylpyrrolidone polymer is present in an amount of from about 1 to about 4 percent by weight based on the weight of the resin, polymer and solvent-carrier.

4. The composition of claim 2 in which the vinylpyrrolidone polymer is present in an amount of from about 1 to about 4 percent by weight based on the weight of the resin, polymer and solvent-carrier.

5. The composition of claim 1 in which the water soluble, reactive polyamide-epichlorohydrin resin is formed by reaction of epichlorohydrin with the polymer formed by reaction of adipic acid and diethylene triamine.

6. The composition of claim 1 in which the total weight of resin and polymer in the composition is from about 1 to about 5 percent by weight based on the total weight of the composition.

7. The composition of claim 4 in which the total weight of resin and polymer in the composition is from about 1 to about 5 percent by weight based on the total weight of the composition.

8. The composition of claim 5 in which the total weight of resin and polymer in the composition is from about 1 to about 5 percent by weight based on the total weight of the composition.

9. A sprayable temporary curl setting composition comprising at least one water soluble, reactive polyamide-epichlorohydrin resin having the formula:

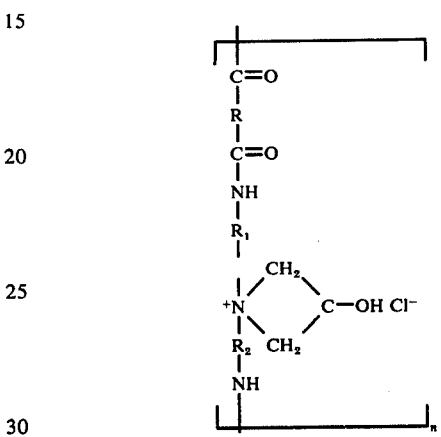

wherein R is an alkyl group containing from 1 to about 6 carbon atoms, $R_1$ and $R_2$ are independently alkyl groups containing from about 2 to about 4 carbon atoms, and n is the number of repeating units in the water soluble molecule and at least one water soluble vinylpyrrolidone polymer dissolved in a solvent-carrier for said resin and polymer, wherein the resin and polymer concentration of said composition are independently from about 0.5 to about 8 percent by weight based on the weight of resin, polymer and solvent-carrier and wherein the weight ratio of resin to polymer is from about 1:2 to about 2:1.

10. The composition of claim 9 in which the resin is present in an amount of from about 1 to about 4 percent by weight based on the weight of resin, polymer and solvent-carrier.

11. The composition of claim 9 in which the vinylpyrrolidone polymer is present in an amount of from about 1 to about 4 percent by weight based on the weight of resin, polymer and solvent-carrier.

12. The composition of claim 10 in which the vinylpyrrolidone polymer is present in an amount of from about 1 to about 4 percent by weight based on the weight of the resin, polymer and solvent-carrier.

13. The composition of claim 9 in which the total weight of resin and polymer in the composition is from about 1 to about 5 percent by weight based on the total weight of the composition.

14. The composition of claim 12 in which the total weight of resin and polymer in the composition is from about 1 to about 5 percent by weight based on the total weight of the composition.

* * * * *